United States Patent [19]

Bugaut et al.

[11] 4,333,730
[45] Jun. 8, 1982

[54] META-PHENYLENEDIAMINES, DYEING COMPOSITIONS IN WHICH THEY ARE PRESENT AND THE CORRESPONDING DYEING PROCESS

[75] Inventors: Andrée Bugaut, Boulogne; Majdi M. Shahin, Paris; Jean-Jacques H. Vandenbossche, Aulray-Sous-Bois; Grégoire Kalopissis, Neuilly sur Seine, all of France

[73] Assignee: Societe Anonyme dite: L'Oreal, Paris, France

[21] Appl. No.: 142,572

[22] Filed: Apr. 18, 1980

[30] Foreign Application Priority Data

Apr. 26, 1979 [FR] France .................. 79 10683

[51] Int. Cl.$^3$ .............................................. A61K 7/13
[52] U.S. Cl. ........................................ 8/407; 8/406; 8/408; 8/409; 8/410; 8/414; 8/416; 8/421; 8/423; 564/347; 564/353; 564/354
[58] Field of Search ................ 8/407, 416, 406, 408, 8/409, 410, 414, 416, 421, 423; 564/350, 347, 353, 354

[56] References Cited

U.S. PATENT DOCUMENTS 4,125,367 11/1978 Bugant et al. ..................... 8/407
4,152,112 5/1979 Bugant et al. ..................... 8/416

Primary Examiner—Donald B. Moyer
Attorney, Agent, or Firm—Cushman, Darby & Cushman

[57] ABSTRACT

Novel meta-phenylenediamines are provided for use as couplers with dye bases in hair dye compositions. These meta-phenylenediamines have the formula:

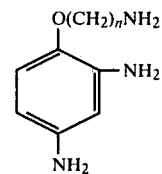

in which n is 2, 3 or 4. Their acid addition salts may also be used.

32 Claims, No Drawings

META-PHENYLENEDIAMINES, DYEING COMPOSITIONS IN WHICH THEY ARE PRESENT AND THE CORRESPONDING DYEING PROCESS

In the field of dyeing keratin fibres, including hair and fur, meta-phenylenediamines have an important function which has been known for a long time; they form part of the class of compounds commonly referred to as "couplers". In association with oxidation bases, such as para-phenylenediamines and para-aminophenols, the couplers give rise, in an oxidizing alkaline medium, to colored indamines, indoanilines or indophenols.

The association of meta-phenylenediamines with para-phenylenediamines, in an oxidizing alkaline medium, gives rise to indamines which are capable of imparting very strong blue colorations to keratin fibres. In association with para-aminophenols, meta-phenylenediamines give rise, in an oxidizing alkaline medium, to indoanilines which impart more or less purplish red colorations to kertain fibres. However, these couplers are in practice few in number. This very small number is explained by the fact that the only compounds which can be singled out for hair dyeing are, on the one hand, those which are very harmless, and, on the other hand, those making it possible to obtain good quality dyeings, that is to say dyeings which do not change in the course of time, or under the action of light, adverse weather conditions or washing.

British Pat. No. 1.548.830 discloses a valuable class of meta-phenylenediamine couplers which can be used in dyeing compositions. The object of the present invention is to describe a new class of meta-phenylenediamines which also make it possible to obtain advantageous results when they are used as couplers in the presence of oxidation bases, such as para-phenylenediamines or para-aminophenols.

The present invention provides a meta-phenylenediamine of the general formula:

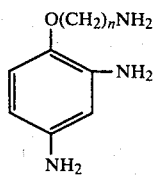

(I)

in which formula n is equal to 2, 3 or 4 and the corresponding salts with acids. Suitable acid addition salts include sulphates, hydrochlorides, citrates and lactates.

From the point of view of harmlessness, the meta-phenylenediamines according to this invention have proved very valuable; in particular 2,4-diaminophenyl β-aminoethyl ether trihydrochloride has been found to be non-mutagenic, in the absence or in the presence of "S9 Mix" induced by "Aroclor 1254", when it was tested on 5 strains of Salmonella typhimurium, namely TA 1538, TA 98, TA 100, TA 1537 and TA 1535.

The present invention also provides a dyeing composition for keratin fibres and in particular for hair, the said composition containing, in a cosmetic carrier, at least one oxidation base and at least one meta-phenylenediamine of the formula (I) as a coupler.

The meta-phenylenediamines with an extranuclear amine group, according to this invention, can be incorporated, in dyeing compositions, with oxidation bases such as:

A. the para-phenylenediamines of the general formula:

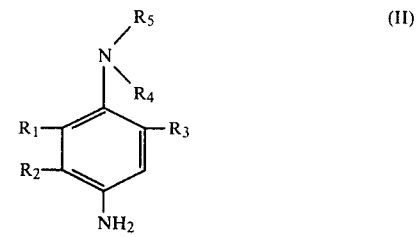

(II)

or the corresponding salts with acids, in which formula $R_1$, $R_2$ and $R_3$ are identical or different and represent a hydrogen atom, an alkyl radical having from 1 to 4 carbon atoms or an alkoxy radical having 1 or 2 carbon atoms, and $R_4$ and $R_5$ are identical or different and represent a hydrogen atom, an alkyl or hydroxyalkyl radical, an alkoxyalkyl radical in which the alkoxy group contains 1 or 2 carbon atoms, or a carbamylalkyl, mesylaminoalkyl, acetylaminoalkyl, ureidoalkyl, carbethoxyaminoalkyl, aminoalkyl, monoalkylaminoalkyl, dialkylaminoalkyl, piperidinoalkyl or morpholinoalkyl radical, the alkyl groups in $R_4$ and $R_5$ having from 1 to 4 carbon atoms, or alternatively $R_4$ and $R_5$ form, together with the nitrogen atom to which they are attached, a piperidino or morpholino group, with the proviso that at least one of $R_1$ and $R_3$ represents a hydrogen atom when neither $R_4$ nor $R_5$ represents a hydrogen atom;

B. the para-aminophenols of the general formula:

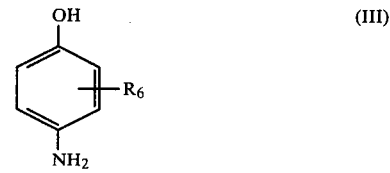

(III)

or the corresponding salts with acids, in which formula $R_6$ represents a hydrogen atom, an alkyl radical containing from 1 to 4 carbon atoms, or a halogen atom, such as, for example, chlorine or bromine; and C. heterocyclic bases, such as 2,5-diaminopyridine, 3-methyl-7-aminobenzomorpholine and 5-aminoindole.

It has been found that the use of the meta-phenylenediamines according to the invention, together with at least one oxidation base referred to above under A, B and C, makes it possible to obtain dyeing composition which impart, to the hair, good quality shades which do not change significantly under the action of light, adverse weather conditions or washing.

Among the compounds of the formula (I) (or their corresponding salts with acids), it has been found that particularly advantageous results can be obtained with 2,4-diaminophenyl β-aminoethyl ether trihydrochloride.

In addition to the coupler (or couplers) of the formula (I) and the associated oxidation base (or bases), the dyeing compositions of the present invention can contain, in particular, the following products, singly or in combination:

(1) other known couplers, for example resorcinol, 2-methylresorcinol, meta-aminophenol, 2-methyl-5- aminophenol, 2-methyl-5-[N-(β-hydroxyethyl)-amino]-phenol, 6-hydroxybenzomorpholine, 2,6-dimethyl-3-acetylaminophenol, 2-methyl-5-carbethoxyaminophenol, 2-methoxy-5-carbethoxyaminophenol, 2-methyl-5-ureidophenol and 1-phenyl-3-methyl-5-pyrazolone;

(2) ortho-phenylenediamines and ortho-aminophenols optionally containing substituents on the nucleus or on the amine groups, and also ortho-diphenol, it being possible for these products to lead to new colored compounds, via complex oxidation mechanisms, either by cyclization with themselves or by reaction with the para-phenylenediamines;

(3) dyestuff precursors of the benzene series, containing, on the nucleus, at least three substituents which are hydroxyl, methoxy or amino groups, such as 2,6-diaminohydroquinone dihydrochloride, 2,6-diamino-4-[N,N-bis-(ethyl)-amino]-phenol trihydrochloride, 2,4-diaminophenol dihydrochloride, 1,2,4-trihydroxybenzene, 2,3,5-trihydroxytoluene or 4-methoxy-2-amino-N-(β-hydroxyethyl)-aniline;

(4) dyestuff precursors of the naphthalene series, such as 2-hydroxy-1,4-naphthoquinone and 5-hydroxy-1,4-naphthoquinone;

(5) leuco-derivatives of indoanilines or of indophenols, such as 4,4'-dihydroxy-2-amino-5-methyldiphenylamine, 4,4'-dihydroxy-2-[N-(β-hydroxyethyl)-amino]-5-methyl-2'-chlorodiphenylamine, 2,4'-diamino-4-hydroxy-5-methyldiphenylamine, 2,4-dihydroxy-4'-[N-(β-methoxyethyl)-amino]-diphenylamine and 2,4-dihydroxy-5-methyl-4'-[N-(β-methoxyethyl)-amino]-diphenylamine;

(6) direct dyestuffs which are nitro benzene dyestuffs, such as 1-[N,N-bis-(β-hydroxyethyl)-amino]-3-nitro-4-(N'-methylamino)-benzene, 1-[N-methyl-N-(β-hydroxyethyl)-amino]-3-nitro-4-[N'-(β-hydroxyethyl)-amino]-benzene, 1-[N-methyl-N-(β-hydroxyethyl)-amino]-3-nitro-4-(N'-methylamino)-benzene, 3-nitro-4-[N-(β-hydroxyethyl)-amino]anisole, 3-nitro-4-[N-(β-hydroxyethyl)-amino]-phenol, 3-nitro-4-aminophenoxyethanol, 3-nitro-4-(N-methylamino)-phenoxyethanol and 2-[N-(β-hydroxyethyl)-amino]-5-nitroanisole; and (7) various customary adjuvants, such as penetrating agents, foaming agents, thickeners, antioxidants, alkalizing or acidifying agents, perfumes, suquestering agents and film-forming products.

The pH of the dyeing compositions according to the invention should be basic, for example from 8 to 11.5. Among the alkalizing agents which can be used, there may be mentioned ammonia, alkylamines, such as ethylamine or triethylamine, alkanolamines, such as mono-, di- or tri-ethanolamine, alkylalkanolamines, such as methyldiethanolamine, sodium hydroxide or potassium hydroxide, and sodium carbonate, potassium carbonate or ammonium carbonate. Among the acidifying agents which can be used, there may be mentioned lactic acid, acetic acid, tartaric acid and phosphoric acid.

Anionic, cationic, non-ionic or amphoteric water-soluble surface-active agents can also be included in compositions according to the invention. Among the surface-active agents which can be used in particular, there may be mentioned alkylbenzenesulphonates, alkylnaphthalenesulphonates, sulphates, ether-sulphates and sulphonates of fatty alcohols, quaternary ammonium salts such as trimethylcetylammonium bromide and cetylpyridinium bromide, diethanolamides of fatty acids, polyoxyethyleneated or polyglycerolated acids and alcohols and polyoxyethyleneated or polyglycerolated alkylphenols. Preferably, the surface-active agents are present in the composition according to the invention in an amount of 0.5 to 55% by weight and advantageously from 4 to 40% by weight, relative to the total weight of the composition.

Organic solvents can also be included in the composition according to the invention in order to solubilize compounds which would otherwise not be sufficiently soluble in water. Among the solvents which can advantageously be used, there may be mentioned ethanol, isopropanol, glycerol, glycols and their ethers, such as 2-butoxyethanol, ethylene glycol, propylene glycol and diethylene glycol monoethyl ether and monomethyl ether. The solvents are advantageously present in the composition in an amount from 1 to 40% by weight and preferably from 5 to 30% by weight, relative to the total weight of the composition.

The thickening products which can be incorporated in the composition according to the invention are advantageously sodium alginate, gum arabic, cellulose derivatives, such as methylcellulose, hydroxyethylcellulose, hydroxypropylmethylcellulose and the sodium salt of carboxymethylcellulose, and acrylic acid polymers; inorganic thickeners, such as bentonite, can also be used. Preferably, the thickeners are present in an amount from 0.5 to 5% by weight and advantageously from 0.5 to 3% by weight, relative to the total weight of the composition.

The antioxidants which can be added to the composition according to the invention include sodium sulphite, thioglycolic acid, mercaptosuccinic acid, sodium bisulphite, ascorbic acid and hydroquinone. These antioxidants are suitable present in the composition in an amount from 0.05 to 1.5% by weight, relative to the total weight of the composition.

At the time of use, the dyeing composition according to the invention can also contain a sufficient amount of oxidizing agents, such as hydrogen peroxide, urea peroxide or per-salts, such as ammonium persulphate. Typically the resulting mixture is left to act on the hair for 10 to 45 minutes at a temperature from ambient temperature to 45° C., the hair is then rinsed, optionally washed and rinsed again, and then dried.

Generally, the meta-phenylenediamines of the formula (I) are present in the dyeing composition according to the invention in an amount from 0.001 to 2.5% by weight, relative to the total weight of the composition.

The dyeing composition according to the invention can be in the form of, for example, a liquid, a cream, a gel or an aerosol or in any other form suitable for dyeing keratin fibres.

The compounds of the formula (I) can be obtained by the following preparative process. In accordance with this process, the nitro group of an acetylated compound of the formula:

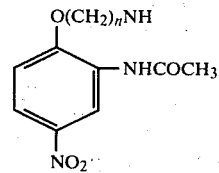

in which n is equal to 2, 3 or 4, is reduced with hydrogen under pressure, in the presence of a catalyst, such as palladium on charcoal, and the resulting product is then deacetylated by means of a hot acid treatment in order to obtain the product of the formula (I).

The following Examples further illustrate the present invention,

EXAMPLE 1

Preparation of 2,4-diaminophenyl-β-aminoethyl ether trihydrochloride

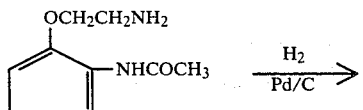

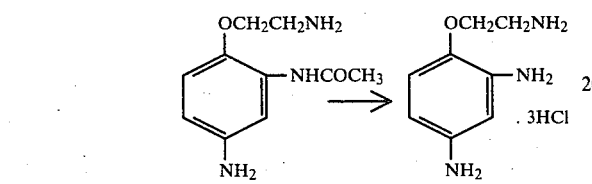

First step:

Preparation of 2-acetylamino-4-aminophenyl β-aminoethyl ether.

The starting product, namely 4-nitro-2-acetylaminophenyl β-aminoethyl ether, is described in Example 9 of the British Patent No. 1.531.605. 12 g (0.05 mol) of 4-nitro-2-acetylaminophenyl β-aminoethyl ether, dissolved in 30 cm³ of absolute alcohol, are reduced using 10% strength palladium-on-charcoal as the catalyst, under a hydrogen pressure of 50 bars, at a temperature of 60° C., for one hour. After filtration through paper, the alcohol is driven off under reduced pressure.

An oil having a theoretical molecular weight of 209 is obtained. The molecular weight found by potentiometric determination in acetic acid, by means of perchloric acid, is 219.8. The oil crystallizes to give a white product having a melting point of 87° C.

Second step:

Preparation of 2,4-diaminophenyl β-aminoethyl ether trihydrochloride 2 g. (0.0087 mol) of 2-acetylamino-4-aminophenyl β-aminoethyl ether are heated in 5 cm³ of hydrochloric acid for 20 minutes on a boiling waterbath. On cooling, the trihydrochloride crystallizes. The product is filtered off, washed with ether and dried in vacuo over KOH. It melts at 280° C. with decomposition.

Elementary analysis of the product gives the following results:

| Analysis | Calculated for $C_8H_{13}N_3O \cdot 3HCl$ | Found |
|---|---|---|
| C % | 34.72 | 34.72 |
| H % | 5.78 | 6.23 |
| N % | 15.19 | 15.00 |
| Cl % | 38.58 | 38.53–38.40 |

EXAMPLE 2

Preparation of 2,4-diaminophenyl γ-aminopropyl ether trihydrochloride

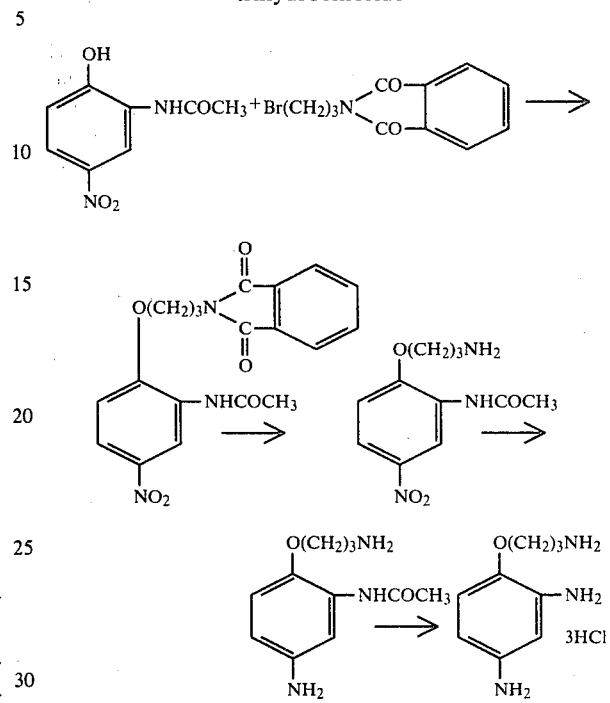

First step:

Preparation of 2-acetylamino-4-nitrophenyl γ-phthalimidopropyl ether 0.17 mol (33.3 g) of 2-acetylamino-4-nitrophenol is dissolved in 170 ml of hexamethylphosphorotriamide. 0.187 mol (26 g) of potassium carbonate and 0.187 mol (50.1 g) of γ-bromopropylphthalimide (melting point: 73° C.) are added to this solution. The reaction mixture is heated on a boiling waterbath for one hour. After cooling, the mixture is poured into 850 cm³ of iced water. The expected product which has precipitated is filtered off. After washing with N/2 sodium hydroxide solution and then with water, and drying in vacuo, the product melts at 214° C.

Second step:

Preparation of 2-acetylamino-4-nitrophenyl γ-aminopropyl ether 0.03 mol (11.5 g) of 2-acetylamino-4-nitrophenyl γ-phthalimidopropyl ether and 3 cm³ of 98% pure hydrazine hydrate in 120 cm³ of normal propyl alcohol are heated for 15 minutes on a boiling waterbath. After hot filtration, the filtrate is cooled to 0° C. The expected product precipitates. It is taken up in a dilute solution of sodium hydroxide, and the sodium hydroxide phase is extracted with chloroform. By concentrating the solvent in vacuo, the expected product, which melts at 110°–120° C., is obtained.

Third step:

Preparation of 2-acetylamino-4-aminophenyl γ-aminopropyl ether 0.026 mol (6.5 g) of 2-acetylamino-4-nitrophenyl γ-aminopropyl ether in 32 cm³ of absolute ethanol is reduced on a 10% strength Pd/C catalyst under a hydrogen pressure of 20 bars, at 80° C., for one hour. After filtration and after cooling the filtrate with a solid carbon dioxide bath, the expected product precipitates.

The product is filtered off and dried in vacuo over P$_2$O$_5$. It melts at 102°–106° C.

Fourth step:

Preparation of 2,4-diaminophenyl γ-aminopropyl ether trihydrochloride 0.00806 mol (1.8 g) of 2-acetylamino-4-aminophenyl γ-aminopropyl ether is heated in 4.5 cm$^3$ of concentrated hydrochloric acid for one hour on a boiling waterbath. On cooling, the expected product precipitates. After being filtered off, washed with ethyl ether and dried in vacuo over KOH, it melts at 260° C. with decomposition. A potentiometric determination is carried out in water by means of N/10 NaOH and the following result is obtained:

calculated theoretical molecular weight: 290.5
molecular weight found: 290.5.

Elementary analysis of the product obtained gives the following results:

| Analysis | Calculated for C$_9$H$_{18}$N$_3$OCl$_3$ | Found |
|---|---|---|
| C % | 37.18 | 37.35 |
| H % | 6.20 | 6.54 |
| N % | 14.46 | 14.32 |
| Cl % | 36.66 | 36.64 |

EXAMPLE 3

The following dyeing composition is prepared:

| | |
|---|---|
| ether trihydrochloride | 0.691 g |
| Para-toluylenediamine dihydrochloride | 0.487 g |
| 2-Butoxyethanol | 5 g |
| Lauryl alcohol containing 10.5 mols of ethylene oxide (per mol of alcohol) | 5 g |
| Ammonia solution (22° B strength) | 10 g |
| Water q.s.p. | 100 g |

The pH of the composition is equal to 10.3.

100 g of hydrogen peroxide of 20 volumes strength are added at the time of use.

When applied to 90% naturally white hair for 20 minutes at 21° C., this mixture imparts to the hair, after rinsing and shampooing, a pure blue coloration.

EXAMPLE 4

The following dyeing composition is prepared:

| | |
|---|---|
| trihydrochloride | 0.276 g |
| 4-[N-(β-hydroxyethyl)-amino]-2-aminophenoxyethanol dihydrochloride | 0.427 g |
| Para-phenylenediamine | 0.270 g |
| 2-Butoxyethanol | 5 g |
| Lauryl alcohol containing 10.5 mols of ethylene oxide | 5 g |
| Ammonia solution (22° B strength) | 10 g |
| Water q.s.p. | 100 g |

The pH of the composition is equal to 10.3.

100 g of hydrogen peroxide of 20 volumes strength are added at the time of use.

When applied to 90% naturally white hair for 25 minutes at 20° C., this mixture imparts to the hair, after rinsing and shampooing, a dark blue-violet coloration.

EXAMPLE 5

The following dyeing composition is prepared:

| | |
|---|---|
| Para-phenylenediamine | 1.2 g |
| Para-aminophenol | 0.07 g |
| 2,4-Diaminophenyl β-aminoethyl ether trihydrochloride | 0.1 g |
| Resorcinol | 0.44 g |
| Meta-aminophenol | 0.195 g |
| Oxyethyleneated oleyl alcohol containing two mols of ethylene oxide | 4.5 g |
| Oxyethyleneated oleyl alcohol containing four mols of ethylene oxide | 4.5 g |
| Oxyethyleneated oleylamine containing 12 mols of ethylene oxide, sold by the Company: "ARMOUR" under the name "ETHOMEEN O$_{12}$" | 4.5 g |
| Diethanolamides of copra fatty acids | 9 g |
| Propylene glycol | 3.6 g |
| 2-Butoxyethanol | 8 g |
| Ethanol | 5.4 g |
| Sodium bisulphite solution (35°B strength) | 1 g |
| Ammonia solution (22° B strength) | 10 g |
| Water q.s.p. | 100 g |

The pH of the composition is equal to 10.0.

100 g of hydrogen peroxide of 20 volumes strength are added at the time of use.

When applied to 90% naturally white hair for 30 minutes at 22° C., this mixture imparts to the hair, after rinsing and shampooing, a deep brown coloration.

EXAMPLE 6

The following dyeing composition is prepared:

| | |
|---|---|
| Para-aminophenol | 0.255 g |
| 2,4-Diaminophenyl β-aminoethyl ether trihydrochloride | 0.638 g |
| Sodium lauryl-sulphate containing two mols of ethylene oxide | 20 g |
| Ethylenediaminetetraacetic acid | 0.2 g |
| Sodium bisulphite solution (35° B strength) | 1 g |
| Ammonia solution (22° B strength) | 10 g |
| Water q.s.p. | 100 g |

The pH of the composition is equal to 10.3.

100 g of hydrogen peroxide of 20 volumes strength are added at the time of use.

When applied to 90% naturally white hair for 25 minutes at 22° C., this mixture imparts to the hair, after rinsing and shampooing, a tamarisk coloration.

EXAMPLE 7

The following dyeing composition is prepared:

| | |
|---|---|
| Para-phenylenediamine | 0.9 g |
| Para-aminophenol | 0.07 g |
| 2,4-Diaminophenyl γ-aminopropyl ether trihydrochloride | 0.06 g |
| Resorcinol | 0.44 g |
| Meta-aminophenol | 0.195 g |
| Oxyethyleneated oleyl alcohol containing two mols of ethylene oxide | 4.5 g |
| Oxyethyleneated oleyl alcohol containing four mols of ethylene oxide | 4.5 g |
| Oxyethyleneated oleylamine containing 12 mols of ethylene oxide, sold by the Company: "ARMOUR" under the name "ETHOMEEN O$_{12}$" | 4.5 g |
| Diethanolamides of copra fatty acids | 9 g |
| Propylene glycol | 3.6 g |
| 2-Butoxyethanol | 8 g |
| Ethanol (96° strength) | 5.4 g |
| Sodium bisulphite solution (35° B strength) | 1 g |
| Ammonia solution (22° B strength) | 10 g |

| | |
|---|---|
| Water q.s.p. | 100 g |

The pH of the composition is equal to 10.2.

100 g of hydrogen peroxide of 20 volumes strength are added at the time of use.

When applied to 90% naturally white hair for 30 minutes at ambient temperature, this mixture imparts to the hair, after rinsing and shampooing, a deep chestnut coloration with a bronze sheen.

EXAMPLE 8

The following dyeing composition is prepared:

| | |
|---|---|
| 2,4-Diaminophenyl γ-aminopropyl ether trihydrochloride | 0,770 g |
| Para-aminophenol | 0.287 g |
| 2-Butoxyethanol | 5 g |
| Lauryl alcohol containing 10.5 mols of ethylene oxide | 5 g |
| Ammonia solution (22° B strength) | 10 g |
| Water q.s.p. | 100 g |

The pH of the composition is equal to 10.0.

100 g of hydrogen peroxide of 20 volumes strength are added at the time of use.

When applied to 90% naturally white hair for 20 minutes at ambient temperature, this mixture imparts to the hair, after rinsing and shampooing, a copper-red coloration.

EXAMPLE 9

The following dyeing composition is prepared:

| | |
|---|---|
| 2,4-Diaminophenyl γ-aminopropyl ether trihydrochloride | 0.845 g |
| Para-phenylenediamine | 0.310 g |
| Sodium lauryl-sulphate containing two mols of ethylene oxide | 20 g |
| Ethylenediaminetetraacetic acid | 0.2 g |
| Sodium bisulphite solution (35° B strength) | 1 g |
| Ammonia solution (22° B strength) | 10 g |
| Water q.s.p. | 100 g |

The pH of the composition is equal to 10.2.

100 g of hydrogen peroxide of 20 volumes strength are added at the time of use.

When applied to 90% naturally white hair for 25 minutes at ambient temperature, this mixture imparts to the hair, after rinsing and shampooing, a dark purplish-blue coloration.

EXAMPLE 10

The following dyeing composition is prepared:

| | |
|---|---|
| 2,4-Diaminophenyl γ-aminopropyl ether trihydrochloride | 0.12 g |
| Meta-aminophenol | 0.45 g |
| Resorcinol | 0.81 g |
| 2-Methyl-5-[N-(β-hydroxyethyl)-amino]-phenol | 0.35 g |
| Para-phenylenediamine | 1 g |
| 2,3-Dimethyl-para-phenylenediamine dihydrochloride | 0.5 g |
| Ortho-aminophenol | 0.25 g |
| Nonylphenol containing 4 mols of ethylene oxide, sold under the name "CEMULSOL NP4" by the Company: "RHONE POULENC" | 21 g |
| Nonylphenol containing nine mols of ethylene oxide, sold under the name "CEMULSOL NP9" by the Company: "RHONE POULENC" | 24 g |
| Oleic acid | 4 g |
| 2-Butoxyethanol | 3 g |
| Ethanol (96° strength) | 10 g |
| The pentasodium salt of diethylenetriamine-pentaacetic acid, sold under the name "MASQUOL DTPA" | 2.5 g |
| Thioglycolic acid | 0.6 g |
| Ammonia solution (22° B strength) | 10 g |
| Water q.s.p. | 100 g |

The pH of the composition is equal to 10.

100 g of hydrogen peroxide of 20 volumes strength are added at the time of use.

When applied to bleached hair for 30 minutes at 27° C., this mixture imparts to the hair, after rinsing and shampooing, a very dark brown coloration.

EXAMPLE 11

The following dyeing composition is prepared:

| | |
|---|---|
| 2,4-Diaminophenyl β-aminoethyl ether trihydrochloride | 2.6 g |
| N-ethyl-N-(β-mesylaminoethyl)-para-phenylenediamine | 2.84 g |
| Sodium lauryl-sulphate containing two mols of ethylene oxide | 20 g |
| Ethylenediaminetetraacetic acid | 0.2 g |
| Sodium Bisulphite solution (35° B strength) | 1 g |
| Ammonia solution (22° B strength) | 10 g |
| Water q.s.p. | 100 g |

The pH of the composition is equal to 9.7.

100 g of hydrogen peroxide of 20 volumes strength are added at the time of use.

When applied to bleached hair for 30 minutes at 30° C., this mixture imparts to the hair, after rinsing and shampooing, a very dark blue-green coloration.

EXAMPLE 12

The following dyeing composition is prepared:

| | |
|---|---|
| 2,4-Diaminophenyl β-aminoethyl ether trihydrochloride | 1.32 g |
| 2-Methylresorcinol | 0.4 g |
| 2-Methyl-5-[N-(β-hydroxyethyl)-amino]-phenol | 0.65 g |
| 6-Hydroxybenzomorpholine | 0.27 g |
| N-(β-Methoxyethyl)-para-phenylene-diamine dihydrochloride | 1.5 g |
| Para-aminophenol | 0.8 g |
| 2-Nitro-4-methyl-6-aminophenol | 1 g |
| Crosslinked polyacrylic acid sold under the name "CARBOPOL 934" by the Company: "GOODRICH CHEMICAL COMPANY" | 3 g |
| Ethanol (96° strength) | 11 g |
| 2-Butoxyethanol | 5 g |
| Trimethylcetylammonium bromide | 2 g |
| Ethylenediaminetetraacetic acid | 0.2 g |
| Ammonia solution (22° B strength) | 10 g |
| Sodium bisulphite solution (35° B strength) | 1 g |
| Water q.s.p. | 100 g |

The pH of the composition is equal to 9.2.

60 g of hydrogen peroxide of 20 volumes strength are added at the time of use.

When applied to naturally light chestnut hair for 20 minutes at 30° C., this mixture imparts to the hair, after rinsing and shampooing, a brown coloration.

EXAMPLE 13

The following dyeing composition is prepared:

| | |
|---|---|
| 2,4-Diaminophenyl β-aminoethyl ether trihydrochloride | 0.005 g |
| 2-Methyl-5-aminophenol | 1.2 g |
| Resorcinol | 0.9 g |
| Meta-aminophenol | 0.7 g |
| 2-Methyl-5-[N-(β-hydroxyethyl)-amino]-phenol | 0.6 g |
| Para-aminophenol | 0.7 g |
| 2,5-Diamino-β-hydroxyethylbenzene dihydrochloride | 3.5 g |
| 3-Nitro-4-aminophenol | 0.8 g |
| Sodium lauryl-sulphate containing two mols of ethylene oxide | 20 g |
| Ethylenediaminetetraacetic acid | 0.2 g |
| Sodium bisulphite solution (d = 1.32) | 1 g |
| Ammonia solution (22° B strength) | 10. g |
| Water q.s.p. | 100 g |

The pH of the composition is equal to 10.4.

100 g of hydrogen peroxide of 20 volumes strength are added at the time of use.

When applied to bleached hair for 20 minutes at 25° C., this mixture imparts to the hair, after rinsing and shampooing, a very coppery chestnut coloration.

EXAMPLE 14

The following dyeing composition is prepared:

| | |
|---|---|
| N-Ethyl-N-(β-hydroxyethyl)-para-phenylenediamine dihydrochloride | 1.83 g |
| 2,4-Diaminophenyl β-aminoethyl ether trihydrochloride | 2 g |
| Oxyethyleneated oleyl alcohol containing two mols of ethylene oxide | 4.5 g |
| Oxyethyleneated oleyl alcohol containing four mols of ethylene oxide | 4.5 g |
| Oxyethyleneated oleylamine containing twelve mols of ethylene oxide, sold under the name "ETHOMEEN O₁₂" | 4.5 g |
| Diethanolamides of copra fatty acids | 9 g |
| Propylene glycol | 4 g |
| 2-Butoxyethanol | 8 g |
| Ethanol (96° strength) | 6 g |
| Pentasodium salt of diethylenetriaminepentaacetic acid, sold under the name "MASQUOL DTPA" | 2 g |
| Hydroquinone | 0.15 g |
| Sodium bisulphite solution 35° B strength) | 1.3 g |
| Ammonia solution (22° B strength) | 10 g |
| Water q.s.p. | 100 g |

The pH of the composition is equal to 9.5.

100 g of hydrogen peroxide of 20 volumes strength are added at the time of use.

When applied to bleached hair for 30 minutes at 27° C., this mixture imparts to the hair, after rinsing and shampooing, a very dark green coloration.

EXAMPLE 15

The following dyeing composition is prepared:

| | |
|---|---|
| 2,4-Diaminophenyl β-aminoethyl ether trihydrochloride | 0.1 g |
| Resorcinol | 0.2 g |
| Meta-aminophenol | 0.2 g |
| 2,6-Dimethyl-3-acetylaminophenol | 0.3 g |
| 2,5-Diaminoisopropylbenzene dihydrochloride | 0.2 g |
| Para-aminophenol | 0.7 g |
| 3-(N-Methylamino)-4-nitrophenoxyethanol | 0.6 g |
| Nonylphenol containing four mols of ethylene oxide, sold under the name "CEMULSOL NP4" by the Company: "RHONE POULENC" | 12 g |
| Nonylphenol containing nine mols of ethylene oxide, sold under the name "CEMULSOL NP9" by the Company: "RHONE POULENC" | 15 g |
| Oxyethyleneated oleyl alcohol containing two mols of ethylene oxide | 1.5 g |
| Oxyethyleneated oleyl alcohol containing four mols of ethylene oxide | 1.6 g |
| Propylene glycol | 6 g |
| Ethylenediaminetetraacetic acid | 0.12 g |
| Thioglycolic acid | 0.6 g |
| Ammonia solution (22° B strength) | 11 g |
| Water q.s.p. | 100 g |

The pH of the composition is equal to 10.

100 g of hydrogen peroxide of 20 volumes strength are added at the time of use.

When applied to bleached hair for 25 minutes at 30° C., this mixture imparts to the hair, after rinsing and shampooing, a coppery coloration.

EXAMPLE 16

The following dyeing composition is prepared:

| | |
|---|---|
| 2,4-Diaminophenyl β-aminoethyl ether trihydrochloride | 0.002 g |
| 2,4-Diaminophenoxyethanol dihydrochloride | 1.2 g |
| Resorcinol | 0.9 g |
| Meta-aminophenol | 0.7 g |
| 2-Methyl-5-aminophenol | 0.6 g |
| 2-Isopropyl-para-phenylenediamine dihydrochloride | 4 g |
| Para-aminophenol | 0.75 g |
| 1-Phenyl-3-methylpyrazol-5-one | 0.25 g |
| 3-Nitro-4-aminophenol | 0.9 g |
| Oxyethyleneated oleyl alcohol containing two mols of ethylene oxide | 4.5 g |
| Oxyethyleneated oleyl alcohol containing four mols of ethylene oxide | 4.5 g |
| Oxyethyleneated oleylamine containing twelve mols of ethylene oxide, sold under the name "ETHOMEEN O₁₂" | 4.5 g |
| Diethanolamides of copra fatty acids | 9 g |
| Propylene glycol | 4 g |
| 2-Butoxyethanol | 8 g |
| Ethanol (96° strength) | 6 g |
| The pentasodium salt of diethylene triamine-pentaacetic acid | 2 g |
| Hydroquinone | 0.15 g |
| Sodium bisulphite solution (35° B strength) | 1.3 g |
| Ammonia solution (22° B strength) | 10 g |
| Water q.s.p. | 100 g |

The pH of the composition is equal to 9.3.

100 g of hydrogen peroxide of 20 volumes strength are added at the time of use.

When applied to 90% naturally white hair for 25 minutes at 27° C., this mixture imparts to the hair, after rinsing and shampooing, a deep chestnut coloration.

EXAMPLE 17

The following dyeing composition is prepared:

| | |
|---|---|
| Para-phenylenediamine | 0.1 g |
| Para-aminophenol | 0.6 g |
| Resorcinol | 0.32 g |
| Meta-aminophenol | 0.32 g |
| 2-Methyl-5-carbethoxyaminophenol | 0.1 g |
| 2,4-Diaminophenyl γ-aminopropyl ether trihydrochloride | 0.05 g |
| 2-Isopropyl-6-nitroaniline | 0.6 g |
| Crosslinked polyacrylic acid sold under the name "CARBOPOL 934" by the Company: "GOODRICH CHEMICAL COMPANY" | 3 g |

| | |
|---|---|
| Ethanol (96° strength) | 11 g |
| 2-Butoxyethanol | 5 g |
| Trimethylcetylammonium bromide | 2 g |
| Ethylenediaminetetraacetic acid | 0.2 g |
| Ammonia solution (22° B strength) | 10 g |
| Sodium bisulphite solution (35° B strength) | 1 g |
| Water q.s.p. | 100 g |

The pH of the composition is equal to 10.

100 g of hydrogen peroxide of 20 volumes strength are added at the time of use.

When applied to 90% naturally white hair for 30 minutes at 30° C., this mixture imparts to the hair, after rinsing and shampooing, a golden deep blond coloration.

EXAMPLE 18

The following dyeing composition is prepared:

| | |
|---|---|
| 2,4-Diaminophenyl β-aminoethyl ether trihydrochloride | 0.075 g |
| 2,4-Diaminophenoxyethanol dihydrochloride | 0.06 g |
| 2,6-Dimethyl-3-acetylaminophenol | 0.48 g |
| 2,3-Dimethyl-para-phenylenediamine dihydrochloride | 0.15 g |
| Para-aminophenol | 0.5 g |
| N-Methyl-para-aminophenol sulphate | 0.32 g |
| 3-Nitro-4-aminophenol | 0.2 g |
| Carboxymethylcellulose | 2 g |
| Ammonium lauryl-sulphate | 5 g |
| Ammonium acetate | 1 g |
| Propylene glycol | 8 g |
| The pentasodium salt of diethylenetriaminepentaacetic acid, sold under the name "MASQUOL DTPA" | 2 g |
| Thioglycolic acid | 0.4 g |
| Triethanolamine | 0.6 g |
| Water q.s.p. | 100 g |

The pH of the composition is equal to 7.9.

60 g of hydrogen peroxide of 20 volumes strength are added at the time of use.

When applied to 90% naturally white hair for 20 minutes at 28° C., this mixture imparts to the hair, after rinsing and shampooing, a copper coloration.

EXAMPLE 19

The following dyeing composition is prepared:

| | |
|---|---|
| 2,4-Diaminophenyl β-aminoethyl ether trihydrochloride | 0.30 g |
| Pyrocatechol | 0.20 g |
| 2,6-Dimethyl-3-acetylaminophenol | 0.10 g |
| 2,5-Diaminopyridine dihydrochloride | 0.6 g |
| 2,6-Dimethyl-para-phenylenediamine dihydrochloride | 0.15 g |
| 3-Nitro-4-[N-(β-hydroxyethyl)-amino]-phenol | 0.06 g |
| Cetyl/stearyl alcohol sold under the name "ALFOL C16/18 E" by the Company: "CONDEA" | 8 g |
| Sodium cetyl-/stearyl-sulphate sold under the name "LANETTE WAX E" by the Company: "HENKEL" | 0.5 g |
| Oxyethyleneated castor oil sold under the name "CEMULSOL B" by the Company: "RHONE POULENC" | 1 g |
| Oleyl diethanolamide | 1.5 g |
| The pentasodium salt of diethylenetriaminepentaacetic acid, sold under the name "MASQUOL DTPA" | 2.5 g |
| Mercaptosuccinic acid | 0.35 g |
| Ammonia solution (22° B strength) | 11 g |
| Water q.s.p. | 100 g |

The pH of the composition is equal to 10.

70 g of hydrogen peroxide of 20 volumes strength are added at the time of use.

When applied to bleached hair for 20 minutes at 30° C., this mixture imparts to the hair, after rinsing and shampooing, a tin grey coloration.

EXAMPLE 20

The following dyeing composition is prepared:

| | |
|---|---|
| 2,4-Diaminophenyl β-aminoethyl ether trihydrochloride | 0.5 g |
| 4-[N,N-(β-Hydroxyethyl)-amino]-aniline dihydrochloride | 0.486 g |
| Nonylphenol containing four mols of ethylene oxide, sold under the name "CEMULSOL NP4" by the Company: "RHONE POULENC" | 21 g |
| Nonylphenol containing nine mols of ethylene oxide, sold under the name "CEMULSOL NP9" by the Company: "RHONE POULENC" | 24 g |
| Oleic acid | 4 g |
| 2-Butoxyethanol | 3 g |
| Ethanol (96° strength) | 10 g |
| The pentasodium salt of diethylenetriaminepentaacetic acid, sold under the name "MASQUOL DTPA" | 2.5 g |
| Thioglycolic acid | 0.6 g |
| Ammonia solution (22° B strength) | 10 g |
| Water q.s.p. | 100 g |

The pH of the composition is equal to 10.

120 g of hydrogen peroxide of 20 volumes strength are added at the time of use.

When applied to 90% naturally white hair for 25 minutes at 27° C., this mixture imparts to the hair, after rinsing and shampooing, a blue-green coloration.

EXAMPLE 21

The following dyeing composition is prepared:

| | |
|---|---|
| Para-phenylenediamine | 0.05 g |
| 2,4-Diaminophenyl γ-aminopropyl ether trihydrochloride | 0.025 g |
| Para-aminophenol | 0.3 g |
| Resorcinol | 0.16 g |
| Meta-aminophenol | 0.16 g |
| 2-Methyl-5-carbethoxyaminophenol | 0.05 g |
| 2-Isopropyl-6-nitroaniline | 0.3 g |
| Oxyethyleneated oleyl alcohol containing two mols of ethylene oxide | 4.5 g |
| Oxyethyleneated oleyl alcohol containing four mols of ethylene oxide | 4.5 g |
| Oxyethyleneated oleylamine containing twelve mols of ethylene oxide, sold under the name "ETHOMEEN O12" | 4.5 g |
| Diethanolamides of copra fatty acids | 9 g |
| Propylene glycol | 4 g |
| 2-Butoxyethanol | 8 g |
| Ethanol (96° strength) | 6 g |
| The pentasodium salt of diethylenetriaminepentaacetic acid, sold under the name "MASQUOL DTPA" | 2 g |
| Hydroquinone | 0.15 g |
| Sodium bisulphite solution (35° B strength) | 1.3 g |
| Ammonia solution (22° B strength) | 10 g |
| Water q.s.p. | 100 g |

The pH of the composition is equal to 10.5.

100 g of hydrogen peroxide of 20 volumes strength are added at the time of use.

EXAMPLE 22

The following dyeing composition is prepared:

| | |
|---|---|
| 2,4-Diaminophenyl β-aminoethyl ether trihydrochloride | 0.7 g |
| 2,6-Dimethyl-para-phenylenediamine dihydrochloride | 0.5 g |
| Para-aminophenol | 0.26 g |
| Resorcinol | 0.3 g |
| 4-Methyl-2-nitro-6-aminophenol | 0.9 g |
| N-Methyl-para-aminophenol sulphate | 0.4 g |
| 2-Methyl-5-[N-(β-hydroxyethyl)-amino]-phenol | 0.3 g |
| Carboxymethylcellulose | 2 g |
| Ammonium lauryl-sulphate | 5 g |
| Ammonium acetate | 1 g |
| Propylene glycol | 8 g |
| The pentasodium salt of diethylenetriamine-pentaacetic acid, sold under the name "MASQUOL DTPA" | 2 g |
| Thioglycolic acid | 0.4 g |
| 2-Butoxyethanol | 8 g |
| Ammonia solution (22° B strength) | 3 g |
| Water q.s.p. | 100 g |

The pH of the composition is equal to 8.6.

100 g of hydrogen peroxide of 20 volumes strength are added at the time of use.

When applied to 90% naturally white hair for 20 minutes at 28° C., this mixture imparts to the hair, after rinsing and shampooing, a coppery mid-chestnut coloration.

We claim:

1. A compound of the formula:

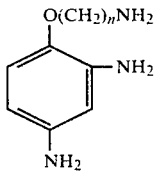

in which n is equal to 2, 3 or 4, or an acid salt thereof.

2. A compound according to claim 1 in which n is equal to 2.

3. 2,4-Diaminophenyl β-aminoethyl ether trihydrochloride.

4. A composition suitable for dyeing human hair in the presence of an oxidizing agent selected from the group consisting of hydrogen peroxide, urea peroxide and ammonium persulfate, said composition comprising an aqueous solution of at least one oxidation base and, as a coupler, at least one compound having the formula

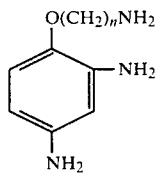

in which n is equal to 2, 3 or 4, or an acid salt thereof.

5. A composition according to claim 4 in which the compound of formula (I) is present in an amount from 0.001 to 2.5% by weight, relative to the total weight of the composition.

6. A composition according to claim 4 having a pH from 8 to 11.5.

7. A composition according to claim 4 in which the oxidation base is a paraphenylenediamine, a para-aminophenol or 2,5-diaminopyridine.

8. A composition according to claim 7 in which the oxidation base is at least one paraphenylene diamine of the general formula:

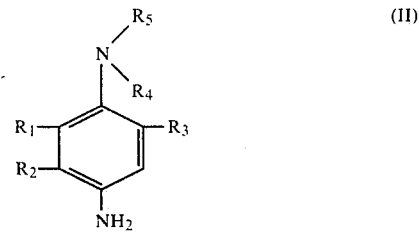

or an acid addition salt thereof in which formula $R_1$, $R_2$ and $R_3$ are identical or different and represent a hydrogen atom, an alkyl radical having from 1 to 4 carbon atoms or an alkoxy radical having 1 or 2 carbon atoms, and $R_4$ and $R_5$ are identical or different and represent a hydrogen atom, an alkyl or hydroxyalkyl radical, an alkoxyalkyl radical in which the alkoxy group contains 1 or 2 carbon atoms, or a carbamyl alkyl, mesylaminoalkyl, acetylaminoalkyl, ureidoalkyl, carbethoxyaminoalkyl, aminoalkyl, monoalkylaminoalkyl, dialkylaminoalkyl, piperidinoalkyl or morpholinoalkyl radical, the alkyl groups in $R_4$ and $R_5$ having from 1 to 4 carbon atoms, or $R_4$ and $R_5$ form, together with the nitrogen atom to which they are attached, a piperidino or morpholino group, with the proviso that at least one of $R_1$ and $R_3$ represents a hydrogen atom when neither $R_4$ nor $R_5$ represents a hydrogen atom.

9. A composition according to claim 7 in which the oxidation base is at least one para-aminophenol of the general formula:

$$\text{(III)}$$

[structure: benzene ring with OH at top, $R_6$ on right side, $NH_2$ at bottom]

or an acid addition salt thereof, in which formula $R_6$ represents a hydrogen atom, an alkyl radical containing from 1 to 4 carbon atoms, or a halogen atom.

10. A composition according to claim 4 which contains at least one of ortho-phenylenediamine, ortho-aminophenol or orthodiphenol.

11. A composition according to claim 4 which contains a leuco-derivative of an indoaniline or indophenol selected from
 4,4'-dihydroxy-2-amino-5-methyldiphenylamine,
 4,4'-dihydroxy-2-[N-(β-hydroxyethyl)-amino]-5-methyl-2'-chlorodiphenylamine,
 2,4'-diamino-4-hydroxy-5-methyl-diphenylamine,
 2,4-dihydroxy-4'-[N-(β-methoxyethyl)-amino]-diphenylamine or
 2,4-dihydroxy-5-methyl-4'-[N-(β-methoxyethyl)-amino]-diphenylamine.

12. A composition according to claim 4 which contains at least one other coupler selected from resorcinol, 2-methylresorcinol, metaaminophenol, 2-methyl-5- aminophenol, 2-methyl-5-[N-(β-hydroxyethyl)-amino]-phenol, 6-hydroxybenzomorpholine, 2,6-dimethyl-3-acetylaminophenol, 2-methyl-5-carbethoxyaminophenol, 2-methoxy-5-carbethoxyaminophenol, 2-methyl-5-ureidophenol or 1-phenyl-3-methyl-5-pyrazolone.

13. A composition according to claim 4 which also contains a dyestuff precursor selected from 2,6-diaminohydroquinone dihydrochloride, 2,6-diamino-4-[N,N-bis-(ethyl)-amino]-phenol trihydrochloride, 2,4-diaminophenol dihydrochloride, 1,2,4-trihydroxybenzene, 2,3,5-trihydroxytoluene or 4-methoxy-2-amino-N-(β-hydroxyethyl)-aniline.

14. A composition according to claim 4 which also contains, relative to the total weight of the composition, from 1 to 40% by weight of an organic solvent to assist in solubilizing the components of said composition said organic solvent being ethanol, isopropanol, glycerol or glycol or an ether thereof.

15. A composition according to claim 4 which also contains relative to the total weight of the composition, from 0.5 to 5% by weight of a thickener which is sodium alginate, gum arabic, methylcellulose, hydroxyethylcellulose, hydroxypropyl-methylcellulose, the sodium salt of carboxymethylcellulose or bentonite.

16. A composition according to claim 4 which also contains, relative to the total weight of the composition, from 0.05 to 1.5% by weight of an antioxidant which is sodium sulphite, thioglycolic acid, mercaptosuccinic acid, sodium bisulphite, ascorbic acid or hydroquinone.

17. Process for dyeing human hair, which comprises, at the time of use, mixing a composition as defined in claim 4 with an oxidizing agent selected from the group consisting of hydrogen peroxide, urea peroxide and ammonium persulfate, applying the mixture to the hair for 10 to 45 minutes at a temperature ranging from ambient temperature to 45° C., rinsing the hair and drying the hair.

18. A composition suitable for dyeing human hair in the presence of at least one oxidizing agent selected from the group consisting of hydrogen peroxide, urea peroxide and ammonium persulphate comprising an aqueous solution of an effective amount of an oxidation base selected from the group consisting of (a) a paraphenylenediamine, (b) 2,5-diaminopyridine and (c) a para-aminophenol and 0.001 to 2.5 percent by weight based on the total weight of the composition of, as a coupling agent, at least one of a member selected from the group consisting of 2,4-diaminophenyl β-aminoethylether, 2,4-diaminophenyl γ-aminopropyl ether, and a salt thereof, said composition having a pH from 8 to 11.5.

19. The composition of claim 18 which also includes an effective amount of another coupling agent selected from the group consisting of resorcinol, 2-methyl resorcinol, meta-aminophenol, 2-methyl-5-N-(β-hydroxyethyl) aminophenol, 2-methyl-5-aminophenol, 6-hydroxybenzomorpholine, 1-phenyl-3-methyl pyrazol-5-one, 2,4-diaminophenoxyethanol, 2-methyl-5-[N-(β-hydroxyethyl)-amino]phenol, 2,6-dimethyl-3-acetylaminophenol and 2-methyl-5-carbethoxy aminophenol.

20. The composition of claim 18 which also contains an effective amount of a direct dye selected from the group consisting of 3-nitro-4-aminophenol, 3-nitro-4-N-(β-hydroxyethyl) aminophenol and 2-nitro-4-methyl-6-aminophenol.

21. The composition of claim 18 which also contains from 0.5 to 50 percent by weight of a water-soluble surface active agent based on the total weight of said composition.

22. The composition of claim 21 wherein said surface active agent is present in an amount of 4 to 40 percent by weight of said composition.

23. The composition of claim 18 which also includes 1 to 40 percent by weight of an organic solvent to assist in solubilizing the components of said composition, said organic solvent being ethanol, 2-butoxy ethanol or propylene glycol.

24. The composition of claim 23 wherein said organic solvent is present in an amount of 5 to 30 percent by weight of said composition.

25. The composition of claim 18 which also includes from 0.5 to 5 percent by weight of a thickening agent based on the total weight of said composition.

26. The composition of claim 25 wherein said thickening agent is present in an amount of 0.5 to 3 percent by weight of said composition.

27. The composition of claim 18 which also contains 0.05 to 1.5 percent by weight of an antioxidant.

28. The composition of claim 27 wherein said antioxidant is selected from the group consisting of thioglycollic acid, sodium bisulphite and hydroquinone.

29. The composition of claim 18 which includes at least one of ortho-aminophenol and pyrocatechol.

30. The composition of claim 18 wherein said oxidation base is (a) a paraphenylenediamine selected from the group consisting of paraphenylenediamine, paratoluylenediamine, 2,6-dimethyl paraphenylenediamine, 2,3-dimethyl paraphenylenediamine, N-(β-methoxyethyl) paraphenylenediamine, N-ethyl-N-(β-hydroxyethyl)paraphenylenediamine, N-ethyl-N-(β-mesylaminoethyl)paraphenylenediamine, 2,5-diaminoisopropylbenzene and 2-isopropylparaphenylenediamine.

31. The composition of claim 18 wherein said oxidation base is para-aminophenol.

32. The composition of claim 18 wherein said oxidation base is 2,5-diaminopyridine.

* * * * *